United States Patent
Muramatsu et al.

(10) Patent No.: US 6,716,169 B2
(45) Date of Patent: Apr. 6, 2004

(54) ULTRASONIC SENSOR, METHOD OF FABRICATING SAME, AND ULTRASONIC DIAGNOSTIC DEVICE USING AN ULTRASONIC SENSOR

(75) Inventors: Hiroyuki Muramatsu, Chiba (JP); Masataka Shinogi, Chiba (JP)

(73) Assignee: Seiko Instruments Inc., Chiba (JP)

( * ) Notice: Subject to any disclaimer, the term of this patent is extended or adjusted under 35 U.S.C. 154(b) by 0 days.

(21) Appl. No.: 09/933,854

(22) Filed: Aug. 20, 2001

(65) Prior Publication Data

US 2002/0103433 A1 Aug. 1, 2002

(30) Foreign Application Priority Data

Aug. 24, 2000 (JP) ........................................ 2000-253250
Aug. 10, 2001 (JP) ........................................ 2001-243943

(51) Int. Cl.$^7$ ................................................ A61B 8/00
(52) U.S. Cl. ........................................ 600/443; 600/459
(58) Field of Search ................................ 600/437, 528, 600/453, 459, 454, 500, 585, 407, 527, 443, 139, 503

(56) References Cited

U.S. PATENT DOCUMENTS

| | | | | |
|---|---|---|---|---|
| 3,847,141 A | * | 11/1974 | Hoop | 600/437 |
| 4,349,032 A | * | 9/1982 | Koyata | 600/139 |
| 4,355,643 A | * | 10/1982 | Laughlin et al. | 600/454 |
| 4,784,152 A | * | 11/1988 | Shinoda et al. | 600/503 |
| 4,794,931 A | | 1/1989 | Yock | |
| 5,000,185 A | | 3/1991 | Yock | |
| 5,058,592 A | * | 10/1991 | Whisler | 600/453 |
| 5,313,949 A | | 5/1994 | Yock | |
| 5,318,035 A | * | 6/1994 | Konno et al. | 600/459 |
| 5,365,937 A | * | 11/1994 | Reeves et al. | 600/528 |
| 5,396,895 A | * | 3/1995 | Takashima et al. | 600/500 |
| 5,522,878 A | * | 6/1996 | Montecalvo et al. | 600/459 |
| 5,575,291 A | * | 11/1996 | Hayakawa et al. | 600/459 |
| 5,579,769 A | * | 12/1996 | Yoshida et al. | 600/437 |
| 5,582,178 A | | 12/1996 | Yock | |
| 5,651,364 A | | 7/1997 | Yock | |
| 5,676,151 A | | 10/1997 | Yock | |
| 5,865,178 A | | 2/1999 | Yock | |
| 5,902,245 A | | 5/1999 | Yock | |
| 6,221,015 B1 | | 4/2001 | Yock | |
| 6,261,237 B1 | * | 7/2001 | Swanson et al. | 600/527 |
| 6,278,890 B1 | * | 8/2001 | Chassaing et al. | 600/407 |
| 6,302,847 B1 | * | 10/2001 | Glenn et al. | 600/459 |
| 6,409,673 B2 | | 6/2002 | Yock | |
| 6,491,647 B1 | * | 12/2002 | Bridger et al. | 600/585 |
| 6,572,554 B2 | | 6/2003 | Yock | |

* cited by examiner

Primary Examiner—Dennis W. Ruhl
Assistant Examiner—Ruby Jain
(74) Attorney, Agent, or Firm—Adams & Wilks (57) ABSTRACT

An ultrasonic diagnostic device has an ultrasonic sensor having a substrate, a piezoelectric element mounted on the substrate for generating an ultrasonic wave to be transmitted into a living body in accordance with an input drive signal, and an intimate contact layer having a first main surface disposed in contact with the piezoelectric element and a second main surface opposite the first main surface for contacting a part of the living body. The intimate contact layer is formed of a flexible material such that the second main surface of the intimate contact layer is brought into close contact with the part of the living body so that no air gaps exist between the second main surface of the intimate contact layer and the part of the living body. A driver circuit generates an input drive signal to drive the piezoelectric element. A biological information detection portion detects biological information relating to the interior of the living body in accordance with the ultrasonic wave transmitted into the living body and an ultrasonic wave reflected from the interior of the living body. A display portion displays the biological information detected by the biological information detection portion.

20 Claims, 9 Drawing Sheets

PRIOR ART

ULTRASONIC SENSOR, METHOD OF FABRICATING SAME, AND ULTRASONIC DIAGNOSTIC DEVICE USING AN ULTRASONIC SENSOR

BACKGROUND OF THE INVENTION

Field of the Invention

The present invention relates to an ultrasonic sensor, a method of fabricating it, and an ultrasonic diagnostic device using such an ultrasonic sensor. More particularly, the invention relates to an ultrasonic sensor for collecting information that gives a measure of a health examination or care such as the thickness of an adipose layer within a living body or the elastic modulus of blood vessels. The invention also relates to a method of fabricating the ultrasonic sensor and to an ultrasonic diagnostic device utilizing the ultrasonic sensor.

Generally, when information about the interior of a living body (such as the thickness of adipose, the elastic modulus of blood vessels, or the shapes of blood vessels) should be collected using an ultrasonic wave, it is necessary to suppress reflections of the ultrasonic wave at the skin to permit the ultrasonic wave to propagate into the body efficiently. Therefore, an oily liquid, or jelly, is interposed between an ultrasonic sensor used in an ultrasonic diagnostic device and the skin. That is, the oily liquid is applied to the skin, and then the ultrasonic sensor is brought into intimate contact with the skin.

Where an oily liquid is applied to the skin, the application operation is cumbersome to perform. Also, another problem occurs, i.e., uncomfortableness such as stickiness is given to the examinee.

For this reason, ultrasonic diagnostic devices that do not need application of oily liquid to the skin have been proposed in recent years. A sensor used in such an ultrasonic diagnostic device (as disclosed in Japanese patent laid-open No. 289554/1995) is described below.

Figure 22:
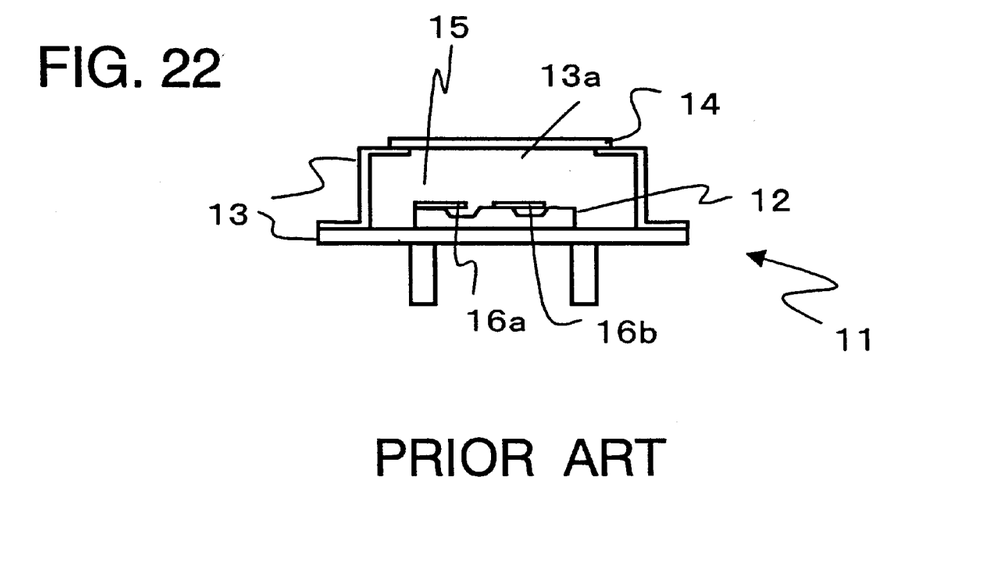
FIG. 22 is a view showing an ultrasonic sensor used in the related art ultrasonic diagnostic device.

FIG. 22 is a cross-sectional view schematically showing the structure of an ultrasonic sensor 11 associated with the prior art ultrasonic diagnostic device. The ultrasonic sensor 11 comprises an ultrasonic oscillator 12 encased in a package 13 made of a metal or other material. The package 13 is provided with an opening window 13a in a location ahead of the ultrasonic oscillator 12. The opening window 13a is coated with an artificial chitinous film 14. The space sealed by the package 13 and the artificial film 14 is filled with silicone oil acting as an ultrasound transmission liquid 15 in which the ultrasonic oscillator 12 is immersed.

The ultrasonic oscillator 12 comprises oscillatory elements 16a and 16b. Any one of them is oscillated for transmission. An ultrasonic wave is sent into the living body from the opening window 13a. The other oscillatory element receives the ultrasonic wave reflected from inside the living body.

The artificial film 14 consisting of a component resembling the skin is used in the portion that is brought into intimate contact with the skin in this way. Consequently, the adhesion to the skin can be enhanced without using oily liquid, and no phase deviation occurs in the ultrasonic wave. As a result, it is not necessary to apply an oily liquid to the skin.

Generally, where an air layer exists between an ultrasonic oscillator and the skin, ultrasonic waves are attenuated by the air layer. This makes it impossible to obtain desired information. Accordingly, in the past, silicone oil has been injected into the package, and the opening window is covered by the artificial film as mentioned above. However, this has the following problems.

(1) If bubbles of air or the like are mixed into the silicone oil, ultrasonic waves are attenuated by the bubbles. Therefore, when the silicone oil is injected into the package, it is necessary to seal the package to prevent intrusion of bubbles. This makes fabrication difficult.

(2) To bring the artificial film into intimate contact with skin wrinkles or the like, it is necessary that the material of the film be comparable in softness with, or superior in softness to, the skin of the human body. If the package is closed using such a material, holes tend to be easily formed in the artificial film in use. Thus, the durability has a problem. Hence, it is difficult to use the film for a long time.

(3) Liquids such as silicone oil generally have high coefficients of thermal coefficient. During use, they expand, causing leakage of silicone oil or varying the path in which ultrasonic waves propagate. This makes it difficult to obtain precise information about the interior of a living body.

SUMMARY OF THE INVENTION

Accordingly, it is an object of the present invention to provide a high-sensitivity ultrasonic sensor that is contacted with the skin with improved adhesion without the necessity of sealing an oily liquid (jelly) or interposing the jelly between the skin and the ultrasonic sensor, as well as an ultrasonic diagnostic device using this ultrasonic sensor.

An ultrasonic sensor associated with an ultrasonic diagnostic device in accordance with the present invention sends out an ultrasonic wave into a living body by driving a piezoelectric element mounted on a substrate according to an input drive signal and receives the wave reflected from inside the living body. An intimate contact layer is formed on the top layer of the piezoelectric element and sticky against the skin of a living body. The ultrasonic sensor is sucked onto the skin of the living body via the intimate contact layer. This structure makes it unnecessary to seal silicone oil or the like. Furthermore, use of any special material is not necessary. An ultrasonic wave can be sent into and received from a living body efficiently without applying an oily liquid between the ultrasonic sensor and the skin.

An ultrasonic wave can be sent into a living body and the reflected wave from inside the living body can be received more effectively by using a material having a Young's modulus ranging from $1.0 \times 10^5$ to $3.0 \times 10^7$ dyne/cm$^2$ as the intimate contact layer.

Substances whose Young's modulus ranging are in the above-described range, i.e., those materials which are preferable as the intimate contact layer, generally show poor adhesion to silicon-based resins, epoxy-based resins, and piezoelectric materials such as PZT. Therefore, the adhesive contact layer showing poor adhesion can be attached to the ultrasonic diagnostic device by giving a mechanism for holding the intimate contact layer to the ultrasonic diagnostic device. The adhesion of the ultrasonic diagnostic device to the skin can be improved. Also, the sensitivity in sending and receiving ultrasonic waves can be enhanced. Furthermore, the treatability can be improved.

A method of fabricating an ultrasonic sensor in accordance with the present invention comprises the steps of: mounting a piezoelectric element on a substrate; mounting an intimate contact layer-holding mechanism to the substrate; and injecting a resin that cures at room temperature, when heated, or irradiated with ultraviolet radiation into the intimate contact layer-holding mechanism and curing the resin. The intimate contact layer can be easily formed by this fabrication method.

An ultrasonic diagnostic device having an ultrasonic sensor is designed to comprise a storage portion for storing an output value when an initial detection is performed and a replacement time-informing portion for comparing information about a living body produced at the time of the initial detection with the currently detected information about the living body and for informing a user of the time when the intimate contact layer should be replaced if a given ratio of the output value (such as a voltage) indicating information about the living body at the time of the initial detection is reached. Consequently, it is possible that the user will be informed of the time when the intimate contact layer should be replaced. Hence, biological information can be measured stably for a long time.

The intimate contact layer can be so constructed that it does not touch the living body when the device is not in use. Alternatively, a protective layer that protects the intimate contact layer when the device is not in use is provided. In this way, the intimate contact layer with low strength can be protected. In consequence, it can be used stably for a long time.

Contaminants such as dust tend to adhere to the surface of members such as silicone gel which are sucked onto the skin of a living body. Therefore, the intimate contact layer is made detachable. If the intimate contact layer is contaminated with dust, it can be replaced with a new intimate contact layer. The ultrasonic diagnostic device can be used stably for a long time while maintaining the sensitivity of the device.

DETAILED DESCRIPTION OF THE PREFERRED EMBODIMENTS

Figure 1A:
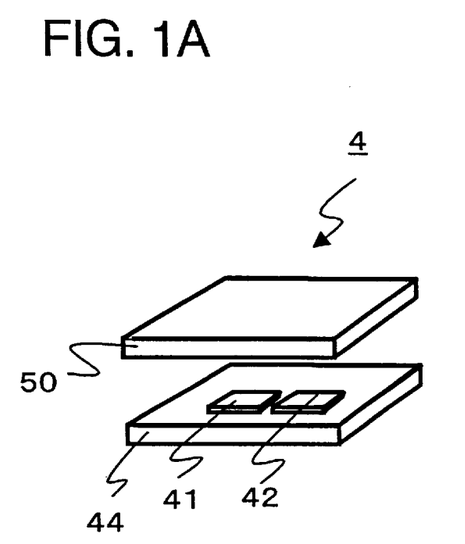
FIG. 1A is a schematic view showing the structure of an ultrasonic sensor in an ultrasonic diagnostic device in accordance with the present invention.
Figure 1B:
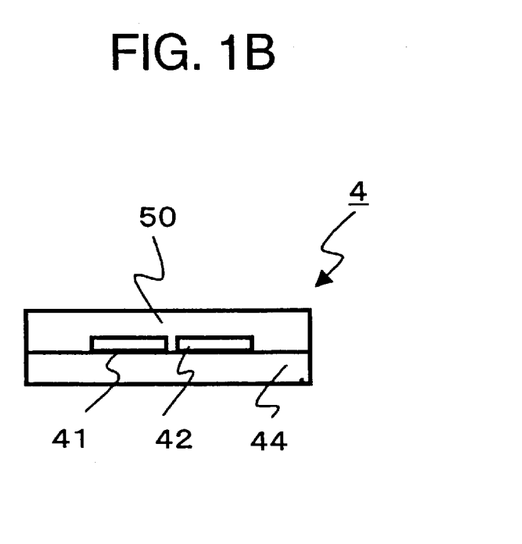
FIG. 1B is a cross-sectional view schematically showing the structure of the ultrasonic sensor in an ultrasonic diagnostic device in accordance with the present invention.

A practiced form of an ultrasonic sensor used in an ultrasonic diagnostic device in accordance with the present invention is described by referring to FIG. 1. FIG. 1A is a perspective view schematically showing the structure of an ultrasonic sensor 4. FIG. 1B is a cross-sectional view schematically showing the ultrasonic sensor 4.

As shown in FIG. 1A, the ultrasonic sensor 4 has a piezoelectric element 41 for transmission and a piezoelectric element 42 for reception. Both piezoelectric elements are mounted on a substrate 44. An intimate contact layer 50 is formed on these piezoelectric elements. A voltage is applied in the direction of thickness of the piezoelectric element 41 for transmission by an electrode and lead wires (not shown), and emits an ultrasonic wave. Information about a living body is obtained by comparing the frequency of the emitted ultrasonic wave with the frequency of the ultrasonic wave received by the piezoelectric element 42 for reception.

If an air gap exists between the living body that is a measured body and the ultrasonic sensor 4, ultrasonic waves are attenuated in the air gap, thus greatly deteriorating the sensitivity. To prevent this, an intimate contact layer 50 is formed between the piezoelectric element and the living body. Preferably, the material of the intimate contact layer 50 is sticky against a living body. Because a living body has minute irregularities such as creases, it is necessary to bring the intimate contact layer into intimate contact with the minute irregularities on the living body. Therefore, it is desired that the material of the intimate contact layer 50 be soft.

Accordingly, the intimate contact layer is fabricated from a material having a Young's modulus of less than $3.0 \times 10^7$ dyne/cm$^2$. Where such a material is used, the detection sensitivity is improved compared with the case in which the intimate contact layer 50 is not used. Especially, silicone rubber and silicone gel that are silicone-based resins match well with living bodies. If they are brought into intimate contact with the skin, it is affected only a little. Therefore, they are excellent materials of the intimate contact layer 50.

By constructing the intimate contact layer 50 in this way, the ultrasonic sensor 4 can be brought into intimate contact with the living body. The air layer existing between the living body and the ultrasonic sensor 4 can be decreased. Attenuation of vibration of ultrasonic waves due to this air layer can be suppressed.

Embodiments of the present invention are hereinafter described with reference to the drawings.

Embodiment 1

Embodiments of an ultrasonic diagnostic device equipped with an ultrasonic sensor in accordance with the present invention are described in detail by referring to FIGS. 2–10.

Figure 2:
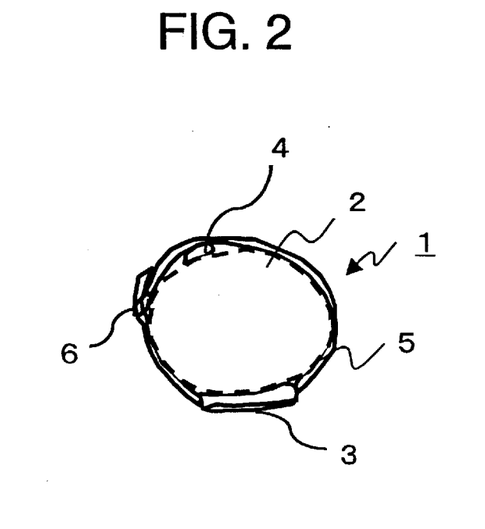
FIG. 2 is a perspective view showing the structure of an ultrasonic diagnostic device to which the present invention is applied.
Figure 3:
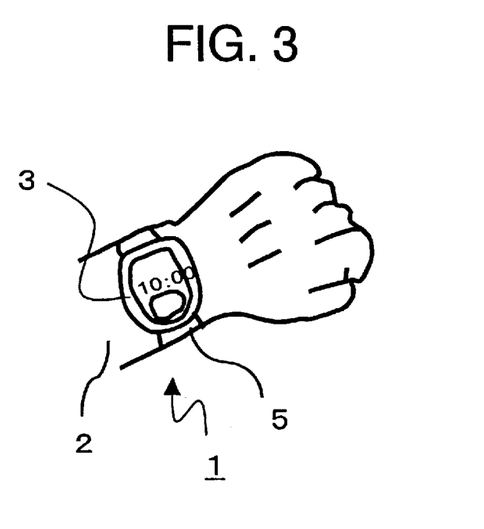
FIG. 3 is a perspective view showing the state in which the ultrasonic diagnostic device in accordance with the invention is worn on a living body (arm)

First, the appearance of the ultrasonic diagnostic device 1 is described by referring to FIGS. 2 and 3.

FIG. 2 is a side elevation schematically showing the appearance of the ultrasonic diagnostic device 1 in accordance with the present invention. The state in which this ultrasonic diagnostic device 1 is attached to a living body 2 (arm) is shown in FIG. 3.

As shown in FIG. 2, the ultrasonic diagnostic device 1 roughly consists of a processing portion 3, an ultrasonic sensor 4, a band 5, and a metal fastening element 6. The ultrasonic diagnostic device 1 is always portable by attaching it to the living body 2, as shown in FIG. 3. The processing portion 3 and the ultrasonic sensor 4 are attached to the band 5, and worn on the living body 2 (broken line portion in the figure) by the band 5 and the metal fastening element 6. At this time, the ultrasonic sensor 4 is placed against the radial artery or against the vicinities of an ulnar vein (not shown) of the living body 2. The processing portion 3 and the ultrasonic sensor 4 are connected together by a lead wire (not shown). A voltage signal for drive is applied to the ultrasonic sensor 4 from the processing portion 3 through this lead wire. A voltage signal measured by the ultrasonic sensor 4 is applied to the processing portion 3.

Figure 4:
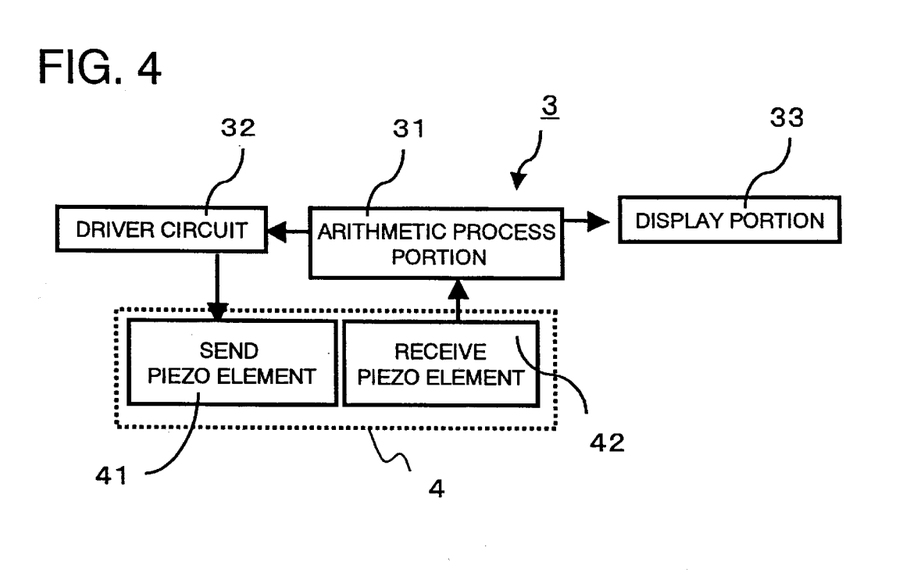
FIG. 4 is a block diagram showing the internal structure of a processing portion and the state in which it is connected with an ultrasonic sensor.

The processing portion of the ultrasonic diagnostic device is next described by referring to FIG. 4, which is a block diagram showing the internal structure of the processing portion 3 and the state in which the processing portion 3 and the ultrasonic sensor 4 are connected. As shown, the processing portion 3 roughly consists of an arithmetic processing portion 31, a driver circuit 32, and a display portion 33.

The arithmetic processing portion 31 executes various kinds of processing regarding detection of pulses by carrying out a processing program stored in a storage region (not shown) incorporated inside the processing portion 31. The results of the processing are displayed on the display portion 33.

During measurement of pulses, the arithmetic processing portion 31 causes the driver circuit 32 to produce a voltage signal for a certain drive to a transmission piezoelectric element 41 (described in detail later) of the ultrasonic sensor 4. Also, the arithmetic processing portion 31 compares the frequency of ultrasonic wave emitted from the transmission piezoelectric element 41 with the frequency of ultrasonic wave varied by the Doppler effect of the blood flow received by a reception piezoelectric element 42 and detects pulse waves.

The driver circuit 32 delivers a voltage signal for a certain drive to the transmission piezoelectric element 41 of the ultrasonic sensor 4 according to instructions from the arithmetic processing portion 31.

The display portion 33 is made of a liquid-crystal viewing screen or the like and displays the results of detection of pulse waves or the like entered from the arithmetic processing portion 31.

Figure 5:
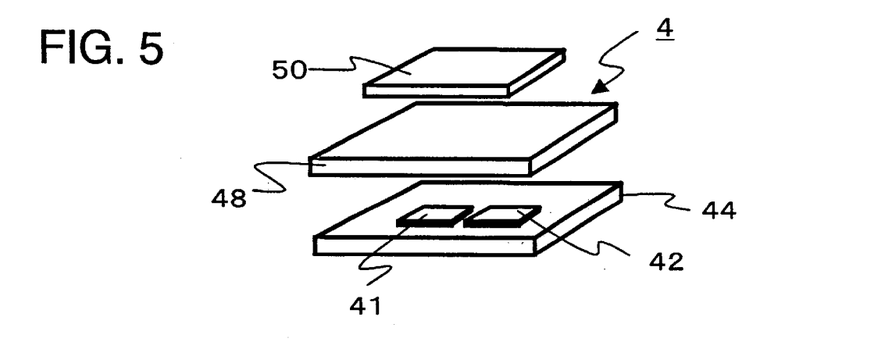
FIG. 5 is a perspective view schematically showing the structure of an ultrasonic sensor in an ultrasonic diagnostic device in accordance with the present invention.
Figure 6:
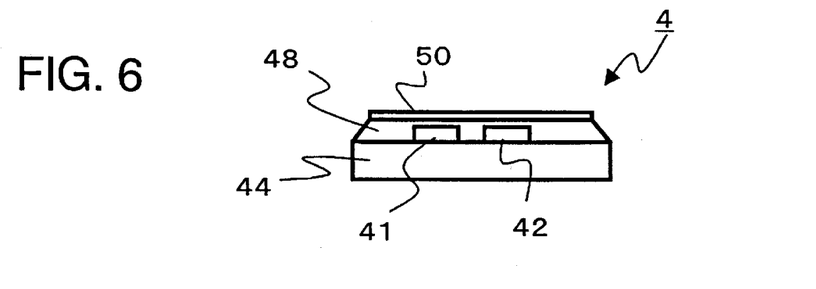
FIG. 6 is a cross-sectional view schematically showing the structure of an ultrasonic sensor in an ultrasonic diagnostic device in accordance with the present invention.

The ultrasonic sensor 4 of the ultrasonic diagnostic device 1 is next described by referring to FIGS. 5 and 6. FIG. 5 is a perspective view schematically showing the ultrasonic sensor 4. FIG. 6 is a view taken from a side of the ultrasonic sensor 4.

As shown in FIG. 5, the ultrasonic sensor 4 roughly consists of the piezoelectric element 41 for transmission, the piezoelectric element 42 for reception, the substrate 44, a matching layer 48, and the intimate contact layer 50.

Electrodes (not shown) are formed on both surfaces of the transmission piezoelectric element 41 and the reception piezoelectric element 42 in the direction of thickness. Voltages can be applied in the direction of thickness of the transmission piezoelectric element 41 and the reception piezoelectric element 42 via lead wires (not shown).

The electrode on the transmission piezoelectric element 41 is connected with the driver circuit 32 of the processing portion 3 by a lead wire (not shown). When a voltage signal for a certain drive is applied to the electrodes on both faces of the transmission piezoelectric element 41 from the driver circuit 32, the transmission piezoelectric element 41 is excited into oscillation and produces an ultrasonic wave of a certain frequency. The wave is sent into the living body (see 2a of FIG. 7). In the present embodiment, the element is excited at 9.6 MHz.

The electrodes formed on both faces of the piezoelectric element 42 for reception are connected with the arithmetic processing portion 31 of the processing portion 3 by lead wires. When the piezoelectric element 42 for reception receives an ultrasonic wave from the living body, the element converts the ultrasonic wave into a voltage signal and sends it to the arithmetic processing portion 31 of the processing portion 3.

Note that a common piezoelectric element may be used for the transmission piezoelectric element 41 and the piezoelectric element 42 for reception. These piezoelectric elements 41 and 42 may be shaped into any desired form. Also, piezoelectric elements of different shapes may be used for transmission and reception. In addition, plural piezoelectric elements 41 for transmission and plural piezoelectric elements 42 for reception may be mounted.

In the present embodiment, PZT having a thickness of 0.2 mm (resonant frequency of 9.6 MHz) and outer dimensions of 0.5×8 mm is used as the piezoelectric element 41 for transmission and as the piezoelectric element 42 for reception. A glass epoxy substrate having a thickness of 1.0 mm and outer dimensions of 4×8 mm is used as the substrate 44.

Figure 7:
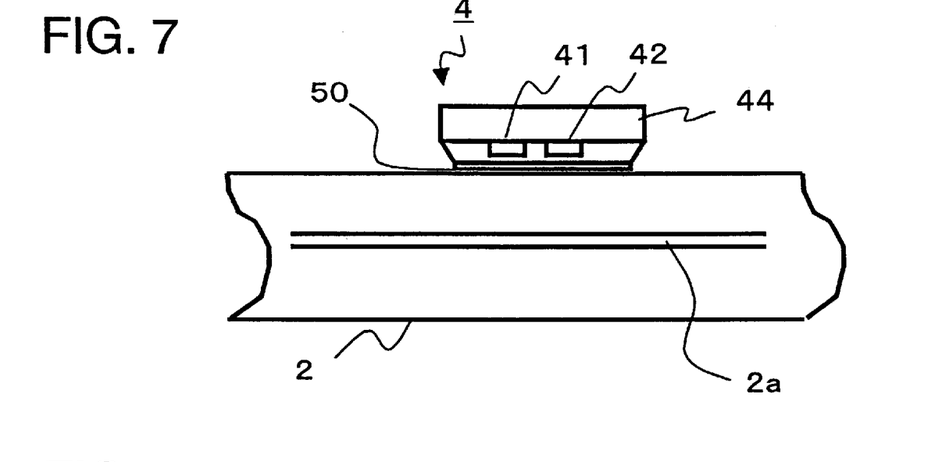
FIG. 7 is a schematic view showing the state in which an ultrasonic sensor is pressed against a living body.

The operation of the processing portion 3 and the ultrasonic sensor 4 in the ultrasonic diagnostic device 1 is next described by referring to FIGS. 4 and 7. FIG. 7 is a view illustrating the positional relation between the ultrasonic sensor 4 and the living body 2 in the ultrasonic diagnostic device in accordance with the present embodiment.

First, as shown in FIG. 7, the ultrasonic diagnostic device 1 is attached to the living body 2 (only the ultrasonic sensor 4 is shown in FIG. 7) such that the sensor 4 is placed against the radial artery or against the vicinities of an ulnar vein of the living body 2. When pulses are detected, the arithmetic processing portion 31 shown in FIG. 4 causes the driver circuit 32 to produce a voltage signal for a certain drive to the electrodes mounted on both faces of the piezoelectric element 41 for transmission.

The piezoelectric element 41 for transmission is excited into oscillation in response to the driving voltage signal applied to the electrodes mounted on both faces, generates an ultrasonic wave, and sends it into the living body 2 (see FIG. 7). The ultrasonic wave sent into the living body 2 is reflected by the blood flow 2a in the artery and received by the reception piezoelectric element 42 in the ultrasonic sensor 4. The piezoelectric element 42 for reception converts the received ultrasonic wave into a voltage signal and sends it to the arithmetic processing portion 31 from the electrodes mounted on both faces.

Then, the arithmetic processing portion 31 compares the frequency of the ultrasonic wave sent from the transmission piezoelectric element 41 with the frequency of the ultrasonic wave varied by the Doppler effect of the blood flow received by the reception piezoelectric element 42 and detects pulse waves in the living body. The arithmetic processing portion 31 displays the results of the detection for the pulse waves on the display portion 33.

In this way, the ultrasonic diagnostic device 1 measures and displays pulse waves in the living body.

A method of fabricating the ultrasonic sensor 4 in accordance with the present embodiment is next described by referring to FIG. 5. Electrodes are formed on both faces of each piezoelectric element, using a metal such as aluminum or Au. The outer shapes are cut by dicing or the like. At this time, the metal such as aluminum or Au is deposited on the surfaces of the piezoelectric elements by vacuum evaporation, for example.

The piezoelectric elements fabricated in this manner are bonded to the substrate 44 as the transmission piezoelectric element 41 and the reception piezoelectric element 42, respectively, by an adhesive or the like.

The electrodes on both faces of the transmission piezoelectric element 41 are connected with the driver circuit 32 of the processing portion 3 of FIG. 4 by lead wires (not shown). The electrodes on both faces of the reception piezoelectric element are connected with the processing circuit 31.

Then, the matching layer 48 is formed on the top surfaces of the transmission piezoelectric element 41 and the reception piezoelectric element 42. Subsequently, the intimate contact layer 50 is formed on the top surface of the matching layer 48. In this way, the ultrasonic sensor 4 is formed.

The material of the matching layer 48 is next described. The matching layer 48 is made of an epoxy-based resin or silicone-based resin, and acts to protect the transmission piezoelectric element 41 and the reception piezoelectric element 42 and to transmit an ultrasonic wave between the living body and each of the piezoelectric elements 41, 42 via the intimate contact layer 50 efficiently.

To propagate an ultrasonic wave between the living body and each of the piezoelectric elements 41, 42 via the intimate contact layer 50 efficiently, it is necessary to set the acoustic impedance of the matching layer 48 to a value between the acoustic impedance Zl of the intimate contact layer and the acoustic impedance Zc of each piezoelectric element. An acoustic impedance is a value indicating the easiness with which acoustic waves are propagated. The value varies depending on the Young's modulus of the material or on the density.

The ideal acoustic impedance Zm of the matching layer 48 in the ultrasonic sensor 4 having the construction shown in FIGS. 5 and 6 is given by $$Zm=(Zc \times Zl)^{1/2} \quad (1)$$

By substituting the acoustic impedance $Zl=1.5 \times 10^6$ (N·sec/m³) of the intimate contact layer (silicone rubber) and Zc (PZT is used)=$30 \times 10^6$ (N.sec/m³) into Eq. (1), we have Zm= about $6.7 \times 10^6$ (N.sec/m³).

If the thickness of the matching layer 48 in the direction of thickness of the substrate is thin, better results arise. In the structure of the present embodiment, values less than 100 μm are desirable. A thermosetting or UV-curable resin is applied to the substrate 44 by spin coating or roller coating. The resin is cured by heat or UV radiation, thus forming the matching layer 48. The matching layer 48 can be arranged with constant thickness and uniformity by this method.

From the considerations given above, an epoxy-based resin having an acoustic impedance of about $3 \times 10^6$ N.sec/m³ is applied to a thickness of about 50 μm and used as the matching layer 48.

The material of the intimate contact layer 50 is next described. If an air gap exists between the living body 2 and the ultrasonic sensor 4, the sensitivity drops severely, because ultrasonic waves are attenuated in the air gap. For this reason, the material of the intimate contact layer 50 is preferably sticky against the living body 2. Furthermore, the living body 2 may have minute irregularities such as creases and so it is necessary to bring the contact layer into intimate contact with the minute irregularities. Therefore, the material of the intimate contact layer 50 is preferably soft. However, if it is too soft, it easily breaks in use and so the durability is poor. Furthermore, it is difficult to shape the material into a desired shape. In this way, problems take place.

To bring the layer into intimate contact with the skin, the material of the intimate contact layer 50 needs to be comparable in softness with the skin or softer than the skin. To represent the hardness of the material (such as rubber or gel) approaching in softness to the skin, a "penetration number" or other value is normally used. However, the value of penetration number varies according to a different standard (such as JIS K2207 and JIS K2220). Therefore, this number cannot be easily used as an index in using the intimate contact layer 50.

Figure 8:
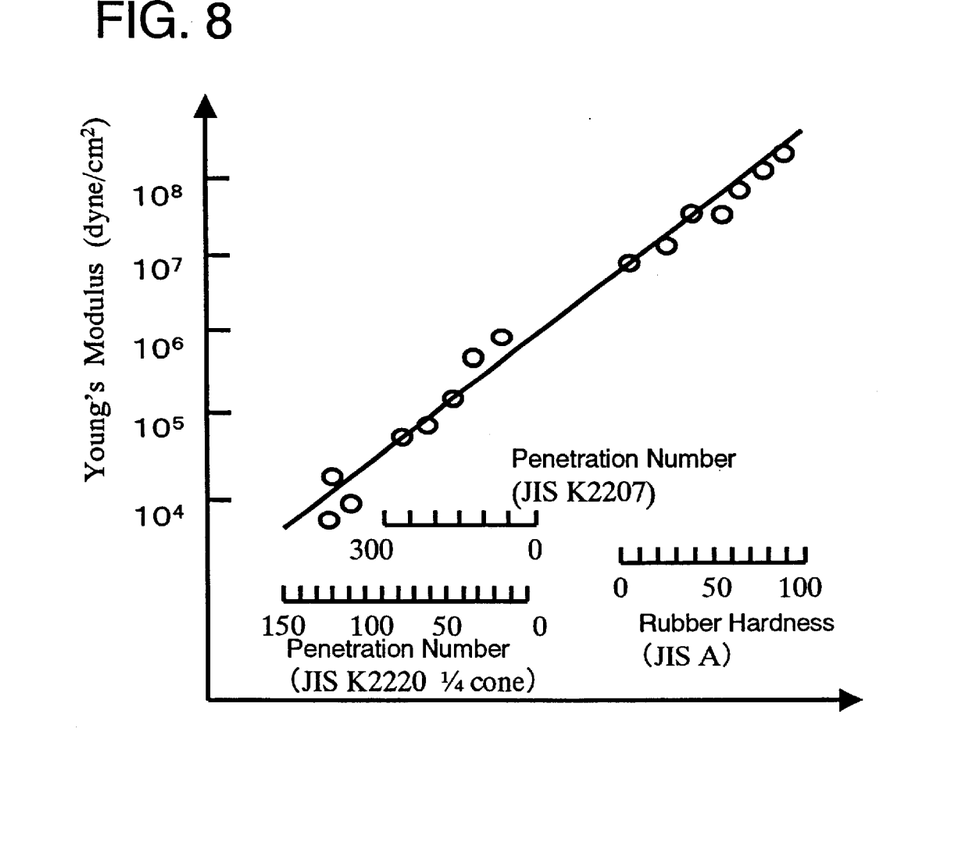
FIG. 8 is a graph illustrating the relation between the material of an intimate contact layer and Young's modulus.

The relation between the "penetration numbers" of silicone rubber and silicon gel that are materials of the intimate contact layer 50 and their Young's moduli is indicated in FIG. 8. The "penetration numbers" and "rubber hardness" according to each standard correspond to their Young's moduli, as shown. The present figure is based on "Silicone Material Handbook", Dow Corning Toray Silicone Co., Ltd.

As shown in FIG. 8, a correlation exists between the penetration number and the Young's modulus. Therefore, Young's modulus can be used as an index in selecting the intimate contact layer 50.

Figure 9:
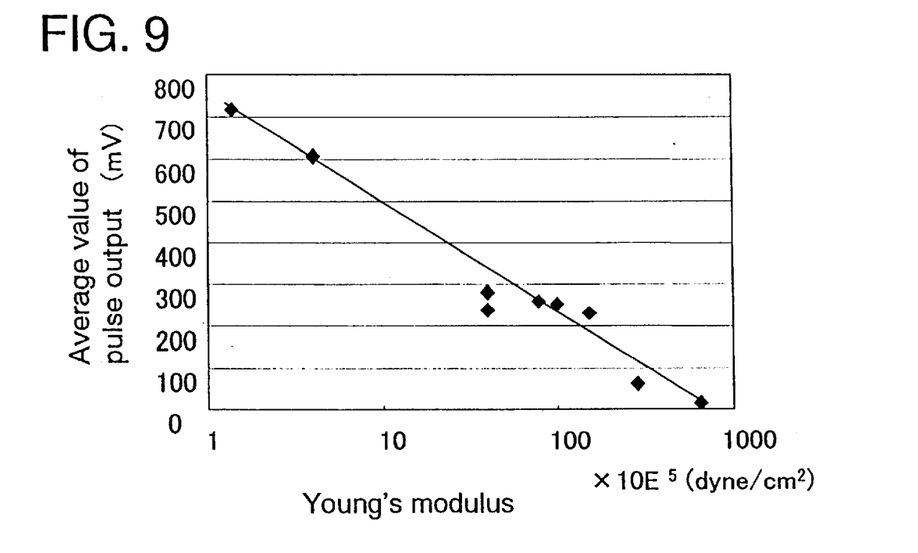
FIG. 9 is a graph illustrating the relation between the material of an intimate contact layer and the sensitivity at which pulses are detected.

FIG. 9 shows the relation between the Young's modulus of the intimate contact layer 50 and the average output value of detected pulses (i.e., the output value from the arithmetic processing portion 31 in FIG. 4) when the material of the intimate contact layer 50 is varied. As can be seen from FIG. 9, the sensitivity with which pulses are detected is improved with lowering the Young's modulus of the intimate contact slayer 50.

In the present embodiment, silicone rubber and silicone gel are used as the material of the intimate contact layer 50.

Figure 10:
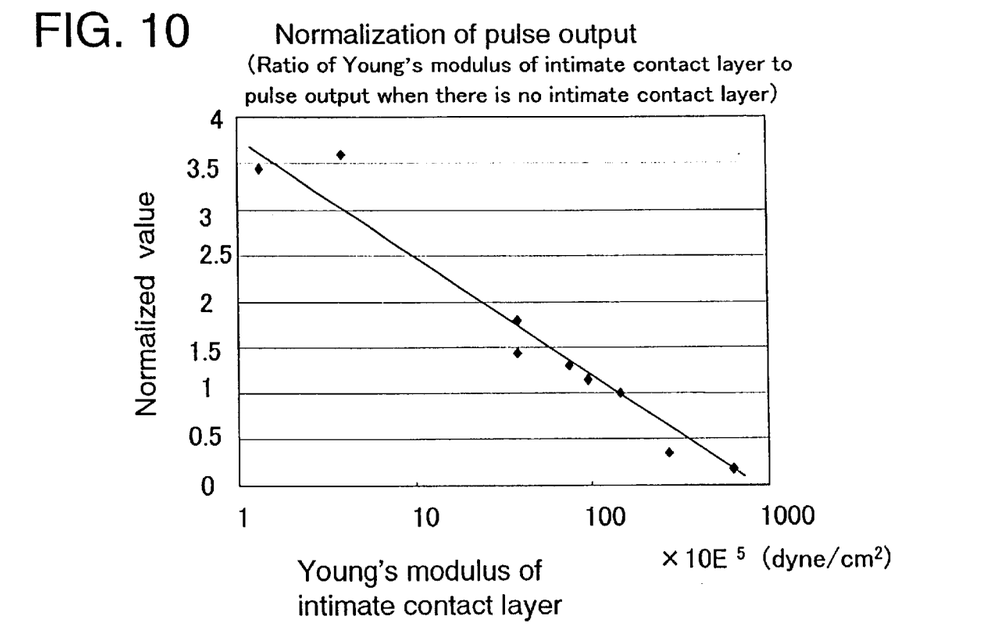
FIG. 10 is a graph illustrating the relation between the material of an intimate contact layer and the sensitivity at which pulses are detected.

FIG. 10 shows the results of FIG. 9, and in which the results where the intimate contact layer 50 is not used are normalized to 1. It can be seen from FIG. 10 that the sensitivity with which pulses are detected is improved in the case where an intimate contact layer having a Young's modulus layer of less than $3.0 \times 10^7$ dyne/cm$^2$ is used compared with the case where the intimate contact layer 50 is not used.

Although results of the case in which the intimate contact layer 50 is made of a material having a Young's modulus of less than $1.0 \times 10^5$ dyne/cm$^2$ are not shown in FIGS. 9 and 10, the intimate contact layer of a material having a Young's modulus of less than $1.0 \times 10^{5 \ dyne/cm^2}$ may be torn off during detection of pulses. Also, it has not been possible to form the intimate contact layer on the matching layer 48 with a uniform thickness.

As the thickness of the intimate contact layer 50 is thin, better results occur. However, if it is too thin, the strength will present problems. Therefore, some thickness is necessary. In the case of the present embodiment, the thickness is set to 0.5 mm.

On the other hand, the acoustic impedances of silicone rubber and silicone gel that have Young's moduli and penetration numbers in the above-described ranges are close to those of the human body and water. Therefore, matching of acoustic impedance poses no problems. In consequence, the ratio of ultrasonic wave reflected at the interface of the intimate contact layer 50 is quite small.

The ultrasonic sensor 4 can be brought into intimate contact with the living body by using the intimate contact layer 50 of the material described above. The air layer existing between the living body and the ultrasonic sensor 4 can be reduced. Attenuation of oscillation of ultrasonic wave due to this air layer can be suppressed. Therefore, the sensitivity to information about the living body is improved.

In the present embodiment, a silicone-based resin is used as the material of the intimate contact layer 50. Silicone-based resins fit living bodies well. If they are brought into intimate contact with the skin, it is affected only a little.

The ultrasonic diagnostic device 1 in accordance with the present embodiment normally measures and displays the pulse. The device can also measure pulse waves.

In the ultrasonic diagnostic device 1 in accordance with the present embodiment, the processing portion 3 and the ultrasonic sensor 4 are spaced from each other. Unlike this, they may be built as one module. This reduces the number of components of the ultrasonic diagnostic device 1 and can suppress the fabrication cost. Additionally, the lead wire between the processing portion 3 and the ultrasonic sensor 4 can be simplified.

A communications portion or the like may be incorporated in the processing portion 3, and the results of measurement of the pulse may be sent to a management system within a hospital. This permits one to monitor the state of a patient wearing the ultrasonic diagnostic device 1 at all times.

Specific portions of the present embodiment are not limited to the specific example described above. Rather, appropriate changes and modifications are possible without departing from the subject matter of the present invention.

For example, in the present embodiment, the excitation frequency of each piezoelectric element is set to 9.6 MHz. Where piezoelectric elements having resonant frequencies of about 8 MHz are used and the excitation frequency is set to about 8 MHz, no problems take place.

Furthermore, in the present embodiment, Young's modulus is used as a measure of the material of the intimate contact layer 50. Where only JIS hardness can be known, intimate contact layers of materials ranging from 0 to 60 (converted from FIG. 8) in the case of JIS-K2220, intimate contact layers of materials ranging from 0 to 200 in the case of JIS-K2207, and intimate contact layers of materials ranging from 0 to 50 in the case of JIS-A may be used.

In the present embodiment, information about the pulse of a living body is measured by the use of the ultrasonic diagnostic device 1. The thickness of an adipose layer within the human body such as the thickness of subcutaneous fat or the thickness of fat in an internal organ may be measured by detecting the phase difference between the sent and received waves. The shape of blood vessels or the elastic modulus of blood vessels may be measured. In this case, the structure holding the processing portion 3 and the structure holding the ultrasonic sensor 4 need to be modified appropriately.

Other embodiments of the ultrasonic sensor that can be used in the ultrasonic diagnostic device described in Embodiment 1 are described in the following Embodiments 2–8. That is, an ultrasonic diagnostic device similar to Embodiment 1 can be accomplished by applying ultrasonic sensors of the following Embodiments 2–8 to those similar to the processing portion, band, fastening element, piezoelectric elements, substrate material, and shape described in Embodiment 1. In the description of the ultrasonic sensor in the following embodiments, the electrodes described in Embodiment 1 are omitted.

Embodiment 2

Figure 11:
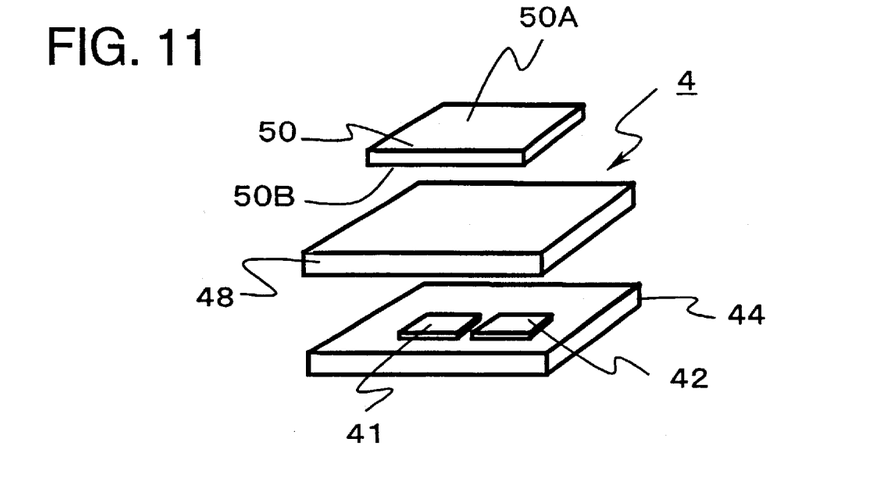
FIG. 11 is a view showing the structure of an ultrasonic sensor in accordance with Embodiment 2 of the present invention.

Another embodiment of an ultrasonic sensor associated with an ultrasonic diagnostic device in accordance with the present invention is described with reference to FIG. 11, which is a perspective view of an ultrasonic sensor 4 associated with an ultrasonic diagnostic device in accordance with the present Embodiment 2.

In the ultrasonic sensor 4 described in Embodiment 1, if the tackiness of the surface (50A in FIG. 11) of the intimate contact layer 50 contacted with the living body is too high, then an unpleasant feeling is given to the user. On the other hand, with respect to the surface (50B in FIG. 11) contacted with the matching layer 48, if the surface has low tackiness, the surface may shift out of position or peel off during use. Accordingly, in the present embodiment, the tackiness of the surface 50A making contact with a living body is set low, while that of the surface 50B making contact with the matching layer 48 is set high. That is, the intimate contact layer is made to have both a layer with high tackiness and a layer with low tackiness. In particular, the layer with high tackiness and the layer with low tackiness may be bonded together. Alternatively, both-sided tape (adhesive layer) may be bonded to the low-tackiness surface 50B of the intimate contact layer 50 to enhance the tackiness of the surface 50B making contact with the matching layer 48. Also, it may be possible to apply a tackiness agent (tackiness layer) such as silicone with low tackiness to the surface 50A of the intimate contact layer 60 with high tackiness to form a low-tackiness layer on the surface 50A making contact with the living body. In the present embodiment, silicone rubber with high tackiness is bonded to the surface 50B of the intimate contact layer 60 to enhance the tackiness of the surface 50B making contact with the matching layer 48.

Desired characteristics can be obtained without giving uncomfortableness to the user by making the surface 50B of the intimate contact layer stickier than the surface 50A.

Embodiment 3

Figure 12A:
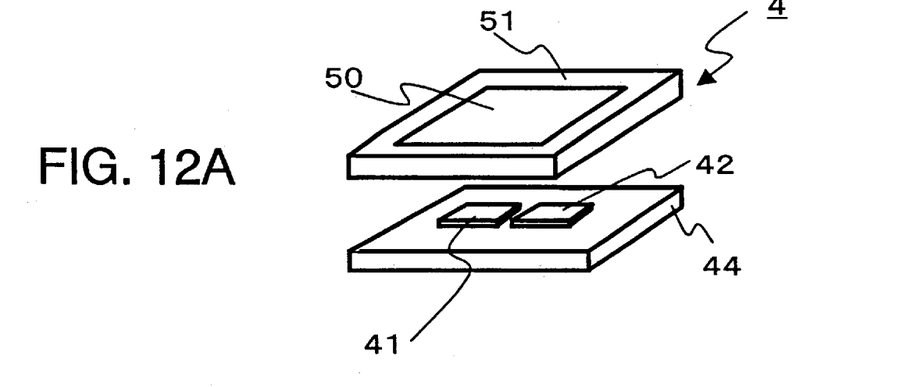
FIG. 12A is a schematic view showing the structure of an ultrasonic sensor equipped with an intimate contact layer-holding mechanism.
Figure 12B:
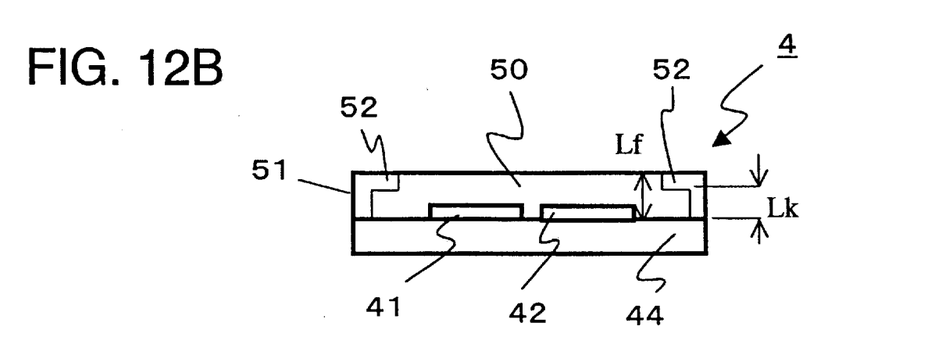
FIG. 12B is a cross-sectional view schematically showing the structure of an ultrasonic sensor equipped with an intimate contact layer-holding mechanism.

Another embodiment of an ultrasonic sensor associated with an ultrasonic diagnostic device in accordance with the present invention is described by referring to FIG. 12. FIG. 12A is a perspective view of an ultrasonic sensor 4 in accordance with the present Embodiment 3. Its cross section is shown in FIG. 12B.

As shown in FIGS. 12A and B, the ultrasonic sensor 4 comprises a piezoelectric element 41 for transmission and a piezoelectric element 42 for reception on the substrate 44, and an intimate contact layer-holding mechanism 51 for holding an intimate contact layer 50. The piezoelectric elements are mounted on a substrate 44. The intimate contact layer-holding mechanism 51 is fixed to the substrate 44.

Generally, as materials such as silicone rubber and silicone gel decrease in hardness (i.e., decrease in Young's modulus), adhesion to glass epoxy substrate, PZT, and other resins decreases. Therefore, it is considered that if the intimate contact layer made of a material whose Young's modulus ranges from $1.0 \times 10^5$ to $3.0 \times 10^7$ dyne/cm$^2$ is used, the intimate contact layer 50 peels off from the piezoelectric elements 41, 42 or from the substrate 44 during use. Therefore, in the present embodiment, the intimate contact layer-holding mechanism 51 has a folded portion 52, as shown in FIG. 12B. This prevents the intimate contact layer 50 from peeling off from the piezoelectric elements 41 and 42. Consequently, the intimate contact layer 50 having a desired Young's modulus that brings the layer into intimate contact with the piezoelectric elements 41, 42 and with the substrate 44 can be formed.

If an air gap exists in the intimate contact layer 50 and in the piezoelectric element 41 for transmission, an ultrasonic wave sent out from the piezoelectric element 41 for transmission is not easily propagated to the intimate contact layer 50. If an air gap is present in the intimate contact layer 50 and in the piezoelectric element 42 for reception, the reflected ultrasonic wave is not easily propagated from the intimate contact layer 50 to the piezoelectric element 42 for reception. In any case, if an air gap exists in the intimate contact layer 50 and in the piezoelectric elements, the sensitivity with which the pulse is detected will drop.

Therefore, in the present embodiment, the intimate contact layer-holding mechanism 51 is constructed as described below. That is, as shown in FIG. 12B, the thickness Lf of the intimate contact layer 50 is set greater than the thickness Lk of the intimate contact layer-holding portion of the intimate contact layer-holding mechanism 51. For example, the intimate contact layer-holding mechanism 51 and the substrate 44 are joined together by applying a pressure in the direction of thickness of the substrate 44. It is possible to avoid creation of any air gap between each piezoelectric element 41, 42 and the intimate contact layer 50. The ultrasonic sensor is brought into contact with the living body, and an ultrasonic wave can be effectively sent into the living body.

In addition, the intimate contact layer 50 can be formed without creating air gap in the piezoelectric elements by forming the piezoelectric elements 41 and 42 on the substrate 44, mounting the intimate contact layer-holding mechanism 51 to the substrate 44, then injecting a resin into the portion of the intimate contact layer-holding mechanism 51 that holds the intimate contact layer, and curing the resin. A thermosetting resin or UV-curable resin can be employed as the resin used herein.

In the present embodiment, acrylic is used as the material of the intimate contact layer-holding mechanism 51. A metal such as Al may also be used.

By providing the mechanism for holding the intimate contact layer in this way, the intimate contact layer does not easily peel off. Biological information can be detected stably for a long time.

Embodiment 4

Figure 13:
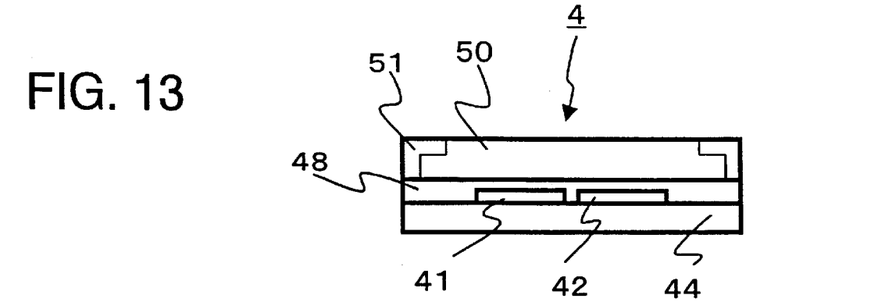
FIG. 13 is a view showing the structure of an ultrasonic sensor in accordance with Embodiment 4 of the present invention.

Another example of an ultrasonic sensor associated with an ultrasonic diagnostic device in accordance with the present invention is described by referring to FIG. 13, which is a cross-sectional view of the ultrasonic sensor 4 in accordance with the present Embodiment 4.

In the present embodiment, the intimate contact layer-holding mechanism 51 described in Embodiment 3 and the matching layer 48 described in detail in Embodiment 1 are combined.

Where an acrylic resin is used as the intimate contact layer-holding mechanism 51 and as the matching layer 48, an ultrasonic sensor of the structure shown in FIG. 13 can be constructed by applying an acrylic-based adhesive between the intimate contact layer-holding mechanism 51 and the matching layer 48. Since the matching layer 48 is formed between the intimate contact layer 50 and each of the piezoelectric elements 41, 42, propagation of ultrasonic wave into a living body is improved, thus improving the sensitivity with which biological information is detected.

Embodiment 5

Figure 14:
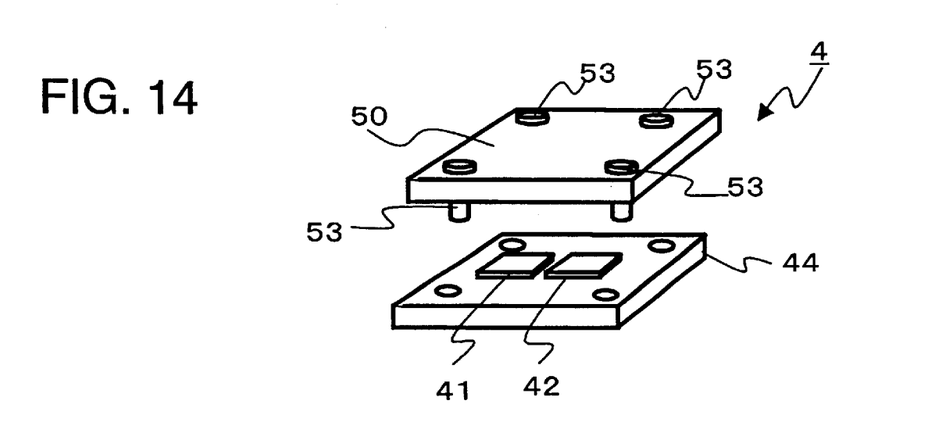
FIG. 14 is a view showing the structure of an ultrasonic sensor in accordance with Embodiment 5 of the invention.

Another example of an ultrasonic sensor associated with an ultrasonic diagnostic device in accordance with the present invention is described by referring to FIG. 14, which is a perspective view of the ultrasonic sensor 4 in accordance with the present Embodiment 5.

As shown in FIG. 14, in the present embodiment, an intimate contact layer-holding mechanism 53 in the form of a pin or screw is used as the intimate contact layer-holding mechanism 51 in accordance with Embodiment 5. By shaping the intimate contact layer-holding mechanism like a pin, the intimate contact layer 50 can be pressed against the piezoelectric elements 41 and 42. Therefore, the intimate contact layer 50 can be brought into intimate contact with the piezoelectric elements 41 and 42 without creating air gaps. An ultrasonic wave can propagate easily from the piezoelectric elements 41 and 42 to the intimate contact layer 50.

Where the intimate contact layer 50 is fouled with dust or dirt, the layer can be used stably for a long time by removing the pin-like intimate contact layer-holding mechanism 54 and replacing it with a new intimate contact layer.

In the same way as in Embodiment 1, a matching layer may be formed between the intimate contact layer 50 and each of the piezoelectric elements 41, 42 to improve the propagation of ultrasonic wave into a living body, thus improving the sensitivity with which biological information is detected.

Embodiment 6

Figure 15:
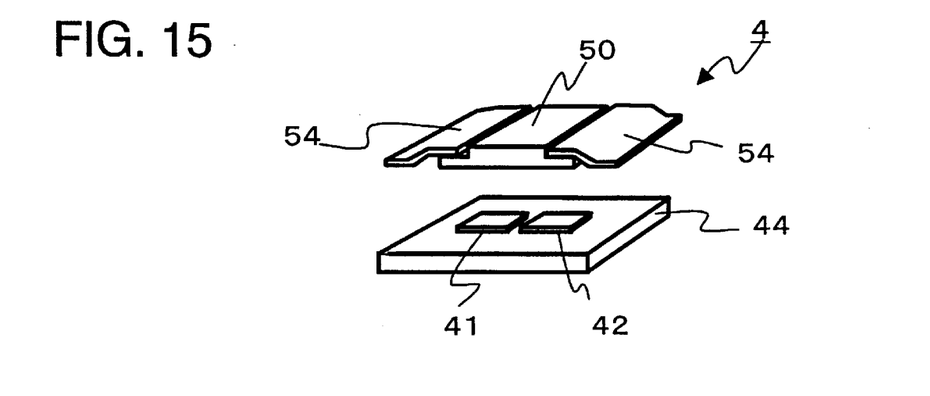
FIG. 15 is a view showing the structure of an ultrasonic sensor in accordance with Embodiment 6 of the invention.

Another embodiment of an ultrasonic sensor associated with an ultrasonic diagnostic device in accordance with the present invention is described by referring to FIG. 15, which is a perspective view of the ultrasonic sensor 4 in accordance with the present Embodiment 6.

As shown in FIG. 15, the intimate contact layer 50 is made convex. A member 54 in the form of a bent plate is used as an intimate contact layer-holding mechanism. The plate-like member 54 and the substrate 44 are joined together by an adhesive, screws (not shown), or the like.

In the present embodiment, the intimate contact layer-holding mechanism is built as the member 54 in the form of a bent plate. The intimate contact layer-holding mechanism prevents the intimate contact layer 50 from assuming a convex form relative to a living body. A structure is achieved in which there is no air gap between the living body and the intimate contact layer 50. This leads to improvement of the sensitivity with which the pulse is detected.

In the same way as in Embodiment 1, a matching layer may be formed between the intimate contact layer 50 and each of the piezoelectric elements 41, 42 to improve the propagation of ultrasonic wave, thus improving the sensitivity with which biological information is detected.

Embodiment 7

Figure 16:
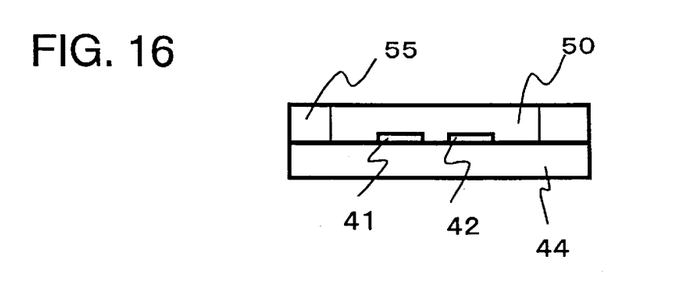
FIG. 16 is a view showing the structure of an ultrasonic sensor in accordance with Embodiment 7 of the invention.

Another example of an ultrasonic sensor associated with an ultrasonic diagnostic device in accordance with the present invention is described by referring to FIG. 16, which is a cross-sectional view of the ultrasonic sensor 4 in accordance with the present Embodiment 7.

Generally, if the Young's modulus of the intimate contact layer 50 deteriorates, adhesion to an epoxy-based resin or the like deteriorates. However, some silicone gels exhibit adhesion to metals such as Al and to glass. Accordingly, in the present embodiment, a resin that shows adhesion to glass and metals is used as the intimate contact layer 50, and the intimate contact layer-holding mechanism 51 is made of glass or a metal.

This structure makes it unnecessary to give uneven portions or a pin-like shape to the intimate contact layer 51. Therefore, a simpler structure can be accomplished. The cost can be curtailed.

The intimate contact layer-holding mechanisms of the shapes described in Examples 3, 4, and 6 may be made of the material in accordance with the present embodiment. The intimate contact layer 50 may also be made of the material in accordance with the present embodiment. Consequently, the intimate contact layer 50 can be held better. Also, propagation of an ultrasonic wave into a living body can be improved.

Embodiment 8

Figure 17:
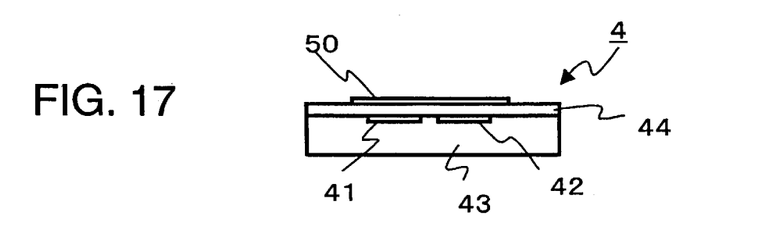
FIG. 17 is a view showing the structure of an ultrasonic sensor in accordance with Embodiment 8 of the invention.

Another embodiment of an ultrasonic sensor associated with an ultrasonic diagnostic device in accordance with the present invention is described by referring to FIG. 17, which is a cross-sectional view of the ultrasonic sensor 4 in accordance with the present Embodiment 8.

In the present embodiment, a piezoelectric element 41 for transmission and a piezoelectric element 42 for reception are mounted on a substrate 44, and an intimate contact layer 50 is formed on the surface (rear surface) of the substrate 44 that faces away from the surface on which the piezoelectric elements are mounted. An acoustic attenuation layer 43 is formed on the surface on which the piezoelectric elements are mounted.

Glass is used as the substrate 44. A resin such as silicone gel that has adhesion to glass is used as the intimate contact layer 50. Hence, intimate contact can be held without using an intimate contact layer-holding mechanism.

In the case of the present embodiment, the substrate 44 needs to satisfy the equation of acoustic impedance described in Embodiment 1. A glass with $1.0 \times 10^7$ N.sec/m$^3$ (Pyrex glass) is used as the substrate 44.

The acoustic attenuation layer 43 needs to suppress ultrasonic wave propagating to the acoustic attenuation layer 43 without permitting propagation of ultrasonic wave from the piezoelectric element 41 for transmission to the substrate 44. Propagation of ultrasonic wave to the acoustic attenuation layer 43 can be prevented by using acrylic resin having a foamed air layer. Foams are injected before curing.

Embodiment 9

Figure 18:
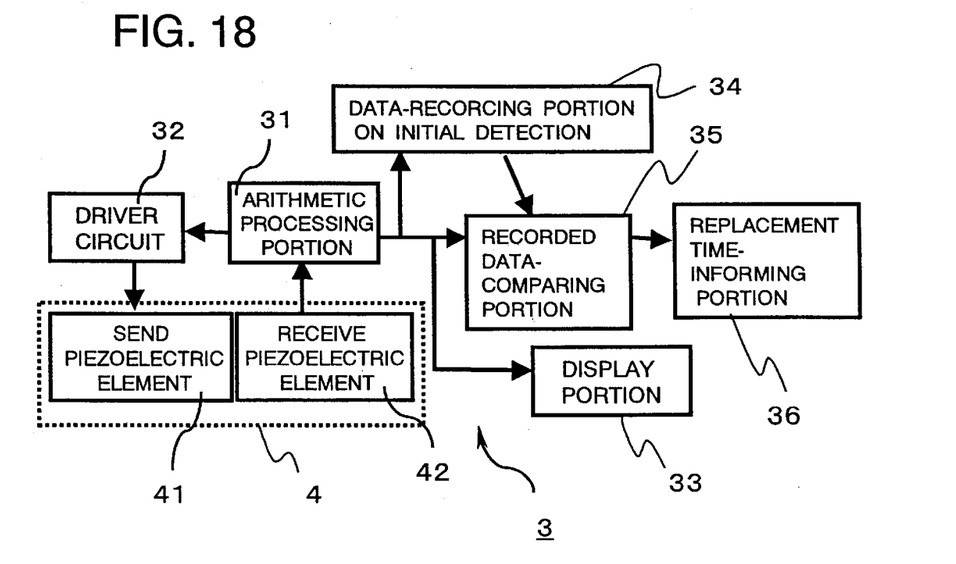
FIG. 18 is a block diagram schematically showing the structure of a processing portion 3 associated with an ultrasonic diagnostic device in accordance with the invention.

An embodiment of an ultrasonic diagnostic device in accordance with the present invention is described by referring to FIG. 18, which is a block diagram schematically showing a processing portion 3 associated with an ultrasonic diagnostic device in accordance with the present embodiment. The same band, fastening element, and so on as used in Embodiment 1 are used. Any of the ultrasonic sensors described above can be used as the ultrasonic sensor 4.

As shown in FIG. 18, the processing portion 3 in accordance with the present embodiment comprises an initial detection time data-recording portion 34, a recorded data-comparing portion 35, and a replacement time-informing portion 36. An arithmetic processing portion 31 detects the difference between the frequency of an ultrasonic wave sent out by a piezoelectric element 41 for transmission and the frequency of an ultrasonic wave received by a piezoelectric element 42 for reception. A voltage value amplified by an amplifier circuit is sent to the recorded data-comparing portion 35 and to a display portion 33.

The output indicative of the pulse detected at the time of initial detection (i.e., when the device is used at first) is recorded in the initial detection time data-recording portion 34. In the case of the present embodiment, this output is a voltage value obtained by detecting the Doppler shifted frequency by the arithmetic processing portion 31 and amplified by an amplifier circuit.

In use, the recorded data-comparing portion 35 compares the output indicative of the presently detected pulse with the output indicative of the initially detected pulse at regular intervals of time.

When the output indicative of the pulse reaches about half the value obtained at the time of initial detection, the replacement time-informing portion 36 informs the user that the intimate contact layer should be replaced. This makes clear the time when the intimate contact layer should be replaced. Therefore, the ultrasonic diagnostic device can be used for a long time without impairing the accuracy at which the pulse is detected.

In the present embodiment, the replacement time-informing portion 36 and the display portion 33 are separate. If the replacement time-informing portion is included in the display portion 33, no problems take place. The data at the time of initial detection is used as data when the ultrasonic diagnostic device is first used. Data derived after 10 minutes or 1 hour may be used to wait until the output indicative of the pulse stabilizes.

Furthermore, the device may be so designed that when the output indicative of the pulse reaches about one-third or one-fourth the value obtained at the time of initial detection, the replacement time-informing portion informs the user that the intimate contact layer should be replaced. Appropriate modifications may be made, depending on the output level indicative of the data produced at the time of initial detection or on the amplification factor by which the signal is amplified by the arithmetic processing portion 31.

Embodiment 10

Figure 19A:
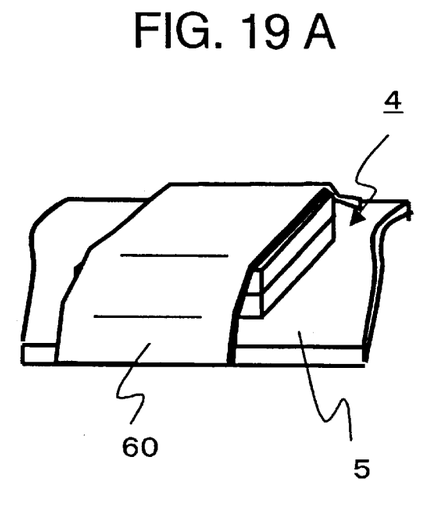
FIG. 19A is a schematic view showing the state of the ultrasonic sensor portion of an ultrasonic diagnostic device in accordance with Embodiment 10 of the invention during nonuse.
Figure 19B:
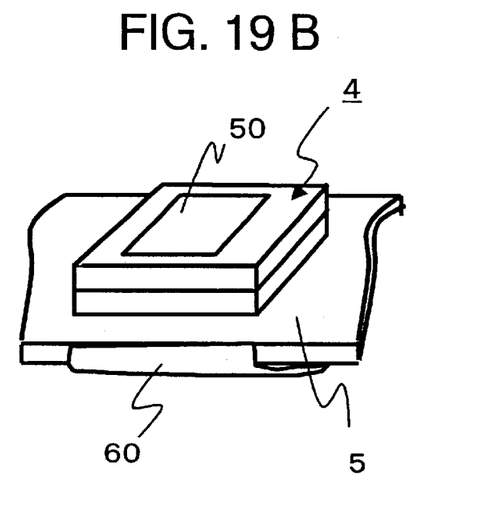
FIG. 19B is a schematic view showing the state of the ultrasonic sensor portion of an ultrasonic diagnostic device in accordance with Embodiment 10 of the invention during use.

Another embodiment of an ultrasonic diagnostic device in accordance with the present invention is described by referring to FIG. 19, which is a view illustrating the structures of ultrasonic sensor 4, band 5, intimate contact layer 50, and intimate contact layer-protecting layer 60 associated with an ultrasonic diagnostic device in accordance with the present invention. Processing portion 3, fastening element, piezoelectric elements, substrate material, and shape are the same as those used in Embodiment 1 described above. Any one of the ultrasonic sensors described above can be used as the ultrasonic sensor 4. FIG. 19A shows the state in which the device is not in use. FIG. 19B shows the state in which the device is in use.

As shown in FIG. 19A, when the device is not in use, the ultrasonic sensor 4 is covered by the intimate contact layer-protecting layer 60. On the other hand, when the device is in use, the intimate contact layer-protecting layer 60 is removed, and the intimate contact layer 50 is exposed, as shown in FIG. 19B.

In the present embodiment, PET film is used as the intimate contact layer-protecting layer 60. Materials other than PET film will present no problems.

In this structure, the intimate contact layer 50 is covered during nonuse. Therefore, dust or dirt does not easily adhere to the intimate contact layer 50. This can improve the durability of the ultrasonic sensor 4. That is, the intimate contact layer with low strength can be protected by providing the protecting layer that protects the intimate contact layer during nonuse. The device can be used stably for a long time.

If stickiness is given to the inner surface of the intimate contact layer-protecting layer 60, dust or dirt adhering to the intimate contact layer 50 can be removed. For instance, a resin having stickiness may be applied to the inner surface of the intimate contact layer-protecting layer 60.

Embodiment 11

Figure 20A:
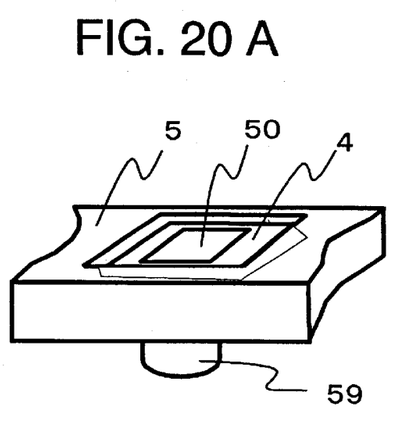
FIG. 20A is a schematic view showing the state of the ultrasonic sensor portion of an ultrasonic diagnostic device in accordance with Embodiment 11 of the invention during nonuse.
Figure 20B:
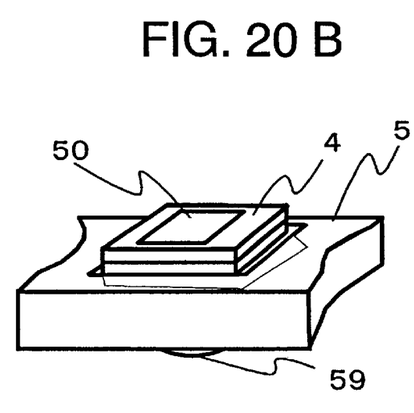
FIG. 20B is a schematic view showing the state of the ultrasonic sensor portion of an ultrasonic diagnostic device in accordance with Embodiment 11 of the invention during use.

Another embodiment of an ultrasonic diagnostic device in accordance with the present invention is described by referring to FIG. 20, which is a view illustrating the structures of ultrasonic sensor 4, band 5, and intimate contact layer 50 associated with an ultrasonic diagnostic device in accordance with the present invention. Processing portion 3, fastening element, piezoelectric elements, substrate material, and shape are the same as those used in Embodiment 1 described above. Any one of the ultrasonic sensors described above can be used as the ultrasonic sensor 4. FIG. 20A shows the state in which the device is not in use. FIG. 21B shows the state in which the device is in use.

As shown in FIG. 20, the ultrasonic sensor 4 is buried in the band 5 and connected with a rod 59. During use, the rod 59 is pushed to protrude the ultrasonic sensor 4 buried in the band 5, as shown in FIG. 20B. Because of this structure, the ultrasonic sensor 4 is not contacted with the skin during nonuse. Therefore, the intimate contact layer 50 of the ultrasonic sensor 4 can be used for a long time. That is, the intimate contact layer is designed not to be contacted with the living body during nonuse. The intimate contact layer with low strength can be protected. In consequence, it can be used stably for a long time.

Embodiment 12

Figure 21:
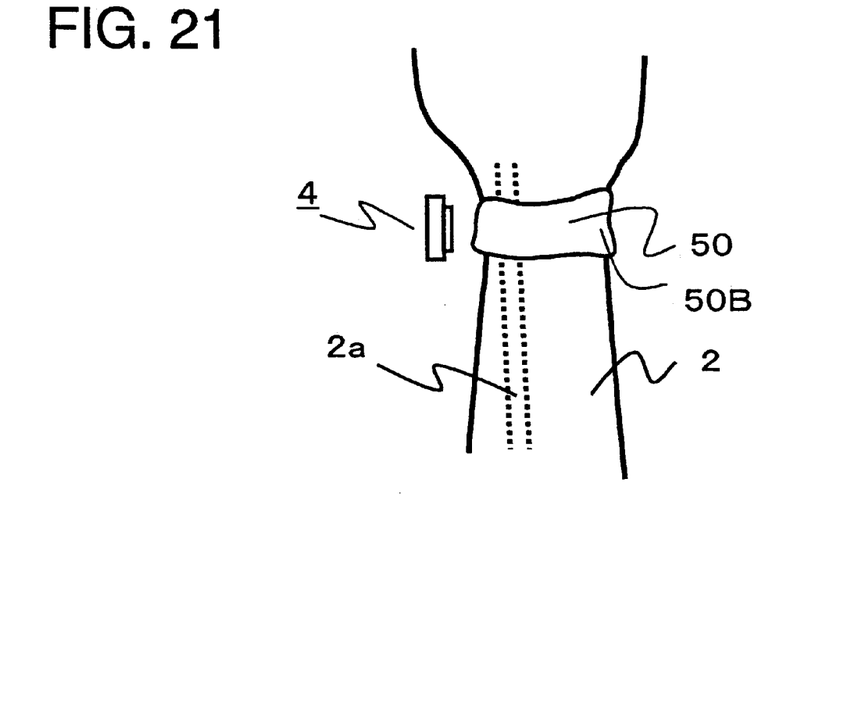
FIG. 21 is a view schematically showing the structure of an ultrasonic diagnostic device in accordance with Embodiment 12 of the invention.

Another embodiment of an ultrasonic diagnostic device in accordance with the present invention is described by referring to FIG. 21, which is a view illustrating the relations among ultrasonic sensor 4, intimate contact layer 50, and living body 2 associated with the ultrasonic diagnostic device in accordance with the present invention. Processing portion, band, fastening element, piezoelectric elements, material of the substrate, and shape can be identical with their respective counterparts of Embodiment 1.

Where replacement of the intimate contact layer is necessary, if the intimate contact layer is attached to the surface of the ultrasonic sensor 4, it is cumbersome to treat the device, because the area of the surface of the ultrasonic sensor making contact with the living body is small. Accordingly, in the present embodiment, as shown in FIG. 21, the intimate contact layer 50 like a band is wound around the living body 2 (a wrist in FIG. 21). The ultrasonic sensor 4 is brought into contact with the wrist from above. A signal indicating the pulse or the like is detected.

The intimate contact layer 50 is wound around the wrist when used. After a lapse of a given usable period, the layer can be replaced with a new intimate contact layer. In order to mount the intimate contact layer 50 to the wrist before use, if the surface of the intimate contact layer 50 contacted with the living body is stickier than the surface 50B contacted with the ultrasonic sensor 4, then the attachment is facilitated. Therefore, in the present embodiment, the surface contacted with the living body is made stickier than the surface 50B contacted with the ultrasonic sensor 4. In particular, a pressure-sensitive adhesive such as silicone is applied to silicone rubber on the surface contacted with the living body.

Because of the structure described thus far, when the intimate contact layer 50 is replaced, desired characteristics can be offered without the need for the user to perform a cumbersome operation. That is, the intimate contact layer is so shaped as to be removable. If dust or dirt adheres to the intimate contact layer, or if the intimate contact layer deteriorates, it can be easily replaced. Hence, it can be used continuously for a long time. If the intimate contact layer is designed to be removable, easy replacement of the intimate contact layer is accomplished by imparting different degrees of stickiness to the front and rear surfaces of the intimate contact layer. Desired biological information can be obtained without the need for the user to perform a cumbersome operation.

It is to be noted that the intimate contact layer is not always required to be formed on the ultrasonic sensor 4 used in the present embodiment. However, a coating layer that protects the piezoelectric elements and their connection is preferably formed. The aforementioned matching layer can be formed on the piezoelectric elements and used as this coating layer.

In the ultrasonic sensor in accordance with the present invention and the ultrasonic diagnostic device using this ultrasonic sensor, a resin (hereinafter referred to as the intimate contact layer) that is sticky against a living body is formed between the living body and each of the piezoelectric elements for transmission and reception, respectively. Therefore, air gap is not easily formed between the ultrasonic sensor and the living body. It is not necessary to apply liquid jelly between the ultrasonic sensor and the living body. This reduces the uncomfortableness given to the user. Furthermore, the sensitivity with which biological information is detected is improved. Additionally, usability and portability are improved.

Furthermore, a replacement time-informing portion having a storage portion for storing the output value produced when initial detection is performed is provided. The replacement time-informing portion compares biological information at the time of initial detection with the presently detected biological information, and informs the user that the intimate contact layer should be replaced when a given ratio has been reached. Consequently, it is possible to inform the user of the time when the intimate contact layer should be replaced. Hence, biological-information can be measured stably for a long time.

What is claimed is:

1. An ultrasonic diagnostic device comprising:

An ultrasonic sensor having a substrate, a piezoelectric element mounted on the substrate for generating an ultrasonic wave to be transmitted into a living body in accordance with an input drive signal, and an intimate contact layer having a first main surface for undergoing sliding contact with the piezoelectric element and a second main surface opposite to the first main surface for contacting a part of the living body, the intimate contact layer being formed of a flexible material such that the second main surface of the intimate contact layer is brought into close contact with the part of the living body so that no air gaps exist between the second main surface of the intimate contact layer and the part of the living body while the first main surface of the intimate contact layer is in sliding contact with the piezoelectric element.

2. An ultrasonic diagnostic device according to claim 1; wherein the intimate contact layer has a Young's modulus in the range of $1.0 \times 10^5$ to $3.0 \times 10^7$ dyne/cm$^2$.

3. An ultrasonic diagnostic device according to claim 1; further comprising a protective layer for protecting the intimate contact layer.

4. An ultrasonic diagnostic device according to claim 1; further comprising a cleaning mechanism for cleaning the intimate contact layer.

5. An ultrasonic diagnostic device according to claim 1; further comprising a holding member for mounting the ultrasonic sensor to the living body; wherein the ultrasonic sensor is movably mounted to the holding member so that an air gap is defined between the ultrasonic sensor and the living body during non-use of the ultrasonic diagnostic device and so that the intimate contact layer of the ultrasonic sensor is disposed in contact with the living body during use of the ultrasonic diagnostic device.

6. An ultrasonic diagnostic device according to claim 1; further comprising an initial detection time data-recording portion for recording biological data obtained during an initial detection by the biological information detection portion of the ultrasonic sensor, a recorded data comparison portion for comparing the recorded biological data with biological information detected during subseguent detection by the biological information detection portion of the ultrasonic sensor, and a replacement time-informing portion for informing a user of the necessity of cleaning or replacement of the intimate contact layer; wherein when a ratio of the biological information to the biological data is less than a preselected value, the replacement time-informing portion informs the user of the necessity of cleaning or replacement of the intimate contact layer.

7. An ultrasonic diagnostic device according to claim 6; the replacement time-informing portion informs the user of the necessity of cleaning or replacement of the intimate contact layer when the detected biological information is less than one-half to one-quarter of the data obtained on initial detection.

8. An ultrasonic diagnostic device according to claim 1; wherein the biological information detected by the biological information detection portion corresponds to a pulse of the living body obtained from the ultrasonic wave transmitted into the living body and from a variation in frequency of the ultrasonic wave reflected by blood flowing through the living body.

9. An ultrasonic diagnostic device comprising:
An ultrasonic sensor having a substrate, a first piezoelectric element mounted on the substrate for generating an ultrasonic wave to be transmitted into an interior of a living body, and a second piezoelectric element for receiving an ultrasonic wave reflected from the interior of the living body;
An intimate contact layer having a first main surface for undergoing sliding contact with the first and second piezoelectric elements of the ultrasonic sensor and a second main surface disposed opposite the first main surface for contacting a part of the living body, the intimate contact layer being formed of a flexible material such that the second main surface of the intimate contact layer is brought into close contact with the part of the living body so that no air gaps exist between the second main surface of the intimate contact layer and the part of the living body while the first main surface of the intimate contact layer is in sliding contact with the piezoelectric element.

10. An ultrasonic diagnostic device according to claim 9; wherein the first main surface of the intimate contact layer comprises an adhesive surface adhered to the ultrasonic sensor with a lesser adhesive force than an adhesive force between the adhesive layer of the intimate contact layer for adhering to the living body.

11. An ultrasonic diagnostic device comprising:
An ultrasonic sensor having a substrate, a first piezoelectric element mounted on the substrate for generating an ultrasonic wave and for transmitting the ultrasonic wave into a part of a living body so that the ultrasonic wave is reflected by blood flowing through an artery in the part of the living body, a second piezoelectric element mounted on the substrate for receding the reflected ultrasonic wave, and a contact layer for undergoing sliding contact with the portion of the substrate over the first and second piezoelectric elements and for direct contact with the part of the living body, the contact layer being made of a material which adheres to the living body when in direct contact therewith so that no air gaps exist between the contact layer and the part of the living body while the contact layer is in sliding contact with the portion of the substrate.

12. An ultrasonic diagnostic device according to claim 11; further comprising a display for displaying the biological information detected by the biological information detection portion.

13. An ultrasonic diagnostic device according to claim 11; further comprising a resin layer disposed between the contact layer and the first and second piezoelectric elements for protecting the first and second piezoelectric elements and for transmitting the ultrasonic wave between the living body and each of the first and second piezoelectric elements via the contact layer.

14. An ultrasonic diagnostic device according to claim 13; wherein the resin layer comprises an epoxy-based resin layer.

15. An ultrasonic diagnostic device according to claim 13; wherein the resin layer comprises a silicone-based resin layer.

16. An ultrasonic diagnostic device according to claim 11; further comprising a protecting layer for protecting the contact layer during non-use of the ultrasonic diagnostic device.

17. An ultrasonic diagnostic device according to claim 11; wherein the biological information detected by the biological information detection portion corresponds to a pulse of the living body.

18. An ultrasonic diagnostic device comprising:
an ultrasonic sensor having a substrate, a first piezoelectric element mounted on the substrate for generating an ultrasonic wave and for transmitting the ultrasonic wave into a part of a living body so that the ultrasonic wave is reflected by blood flowing through an artery in the part of the living body, and a second piezoelectric element mounted on the substrate for receiving the reflected ultrasonic wave;

a contact layer integrally connected to the substrate and having a first main surface disposed over the first and second piezoelectric elements and a second surface for direct contact with the part of the living body;

connecting means for integrally connecting the contact layer to the substrate so that no air gaps exist between the second surface of the contact layer and the part of the living body when the second surface of the contact layer is in direct contact with the part of the living body, a driver circuit for generating an input drive signal to drive the piezoelectric element to generate the ultrasonic wave; and a biological information detection portion for detecting biological information corresponding to the living body by comparing a frequency of the ultrasonic wave transmitted by the first piezoelectric element with a frequency of the reflected ultrasonic wave received by the second ultrasonic element.

19. An ultrasonic diagnostic device according to claim 18; wherein the connecting means comprises a pair of plate members integrally connected to the contact layer and the substrate.

20. An ultrasonic diagnostic device according to claim 19; wherein the contact layer has a pair of stepped portions each integrally connected to a respective one of the plate members.

* * * * *